United States Patent [19]

van der Jagt

[11] Patent Number: Plant 6,005

[45] Date of Patent: Sep. 8, 1987

[54] CHRYSANTHEMUM PLANT NAMED 'REYELLOW'

[75] Inventor: Martinus van der Jagt, Ter Aar, Netherlands

[73] Assignee: Chrysanthemum Breeders Association, N.V., Willemstad, Netherlands Antilles

[21] Appl. No.: 599,979

[22] Filed: Apr. 12, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

A new and distinct cultivar of Chrysanthemum plant named "Reyellow", bearing medium sized yellow blooms with a green yellow center and having a performance of four weeks.

3 Drawing Figures

BACKGROUND OF THE INVENTION

The present invention comprises a new and distinct cultivar of Chrysanthemum plant which is a cross of unknown parents. The invention was discovered by Martinus van der Jagt in May 1982 at Paradysweg 88, Ter Aar, Holland. The invention has been asexually reproduced by cuttings at the same location. The new cultivar has been found to retain its distinctive characteristics through successive propagations.

SUMMARY OF THE INVENTION

The present invention is a new and distinct variety of Chrysanthemum of medium size blooms and a vivid yellow color.

BRIEF DESCRIPTION OF THE DRAWINGS

The present invention of a new and distinct variety of Chrysanthemum is shown in the accompanying drawings, the color being as nearly true a possible with color photographs of this type.

DESCRIPTION OF THE INVENTION

Figure 1:
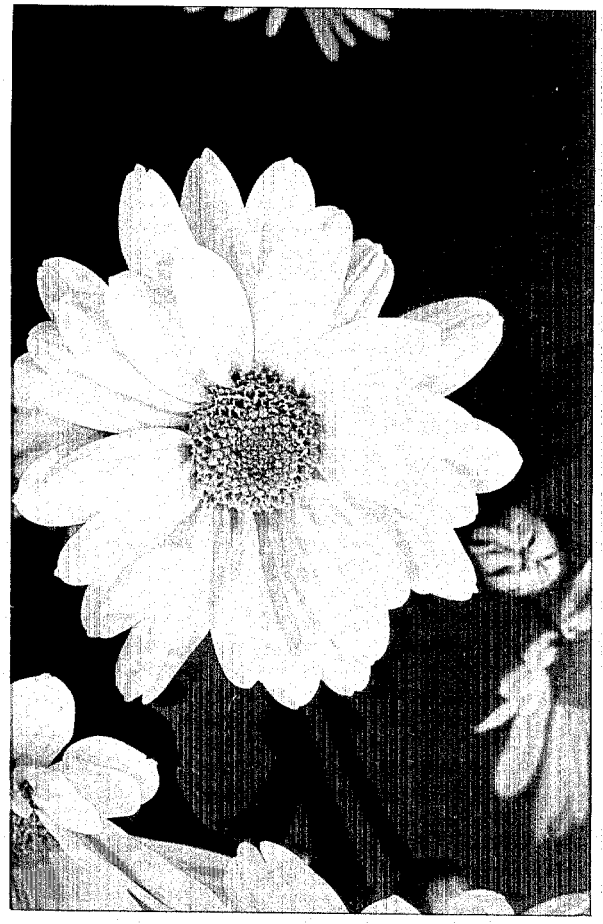
FIG. 1 shows the full bloom of the new cultivar.
Figure 2:
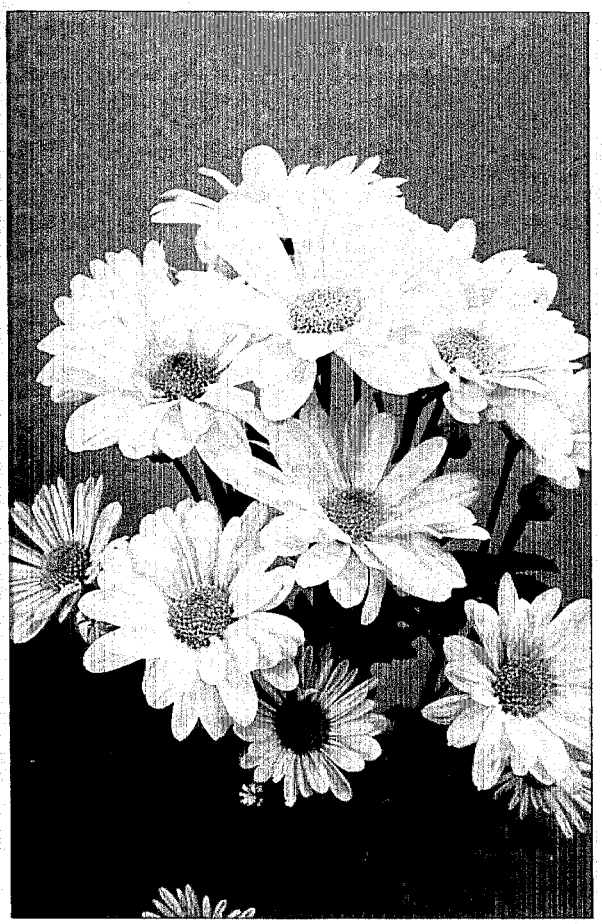
FIG. 2 shows various stages of bloom of the new cultivar.
Figure 3:
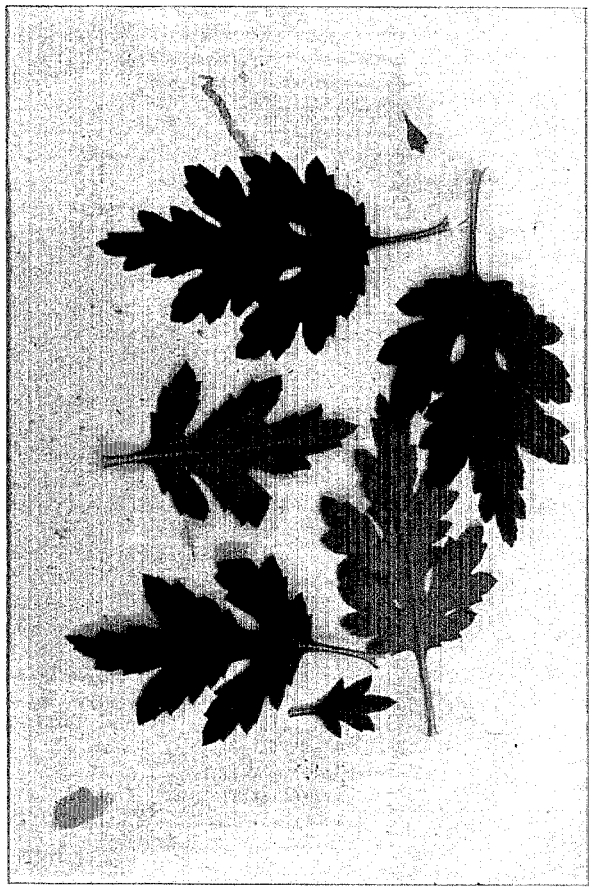
FIG. 3 shows the foliage and stem of the new cultivar.

This new variety of Chrysanthemum is of the botanical classification *Chrysanthemum morifolium*, named "Reyellow". When grown in the vicinity of, Ter Aar, Holland, it has a response time of approximately 8½ weeks. This new variety produces medium sized vivid yellow blooms with a green yellow center having a four week permanence. This new variety of Chrysanthemum has been found to retain its distinctive characteristics throughout successive propagations and may be grown year round under greenhouse conditions.

The following is a description of the plant and characteristics that distinguish it over related known varieties and its antecedents:

Bud:
- *Size.*—Medium.
- *Form.*—High form.
- *Color.*—Bronze yellow (R.H.S. 606).

Botanical classification: *Chrysanthemum morifolium.*

Bloom:

- *Size.*—Medium.
- *Fully open.*—8 cm.
- *Borne.*—Mostly single to 3 flowers.
- *Stems.*—Strong.
- *Form.*—Single.
- *Permanence.*—4 weeks.

Color:
- *Center of flower.*—Uranium green (R.H.S. 63).
- *Base of petals.*—Canary yellow (R.H.S. 2).
- *Inside of petals.*—Canary yellow (R.H.S. 2).
- *Reverse of petals.*—Canary yellow (R.H.S. 2/2).
- *Outer petals.*—Canary yellow (R.H.S. 2).
- *Tonality from a distance.*—A vivid yellow.
- *Discoloration.*—Some to bright yellow (R.H.S. 2/2).

Petals:
- *Texture.*—Rough on the upper side and smooth on the underside.
- *Number.*—26–34.
- *Arrangement.*—Imbricated.
- *Persistence.*—Good, only a little reflexion.
- *Fragrance.*—Typical Chrysanthemum.

Reproductive organs:
- *Stamens.*—Small, normal quantity.
- *Pollen.*—A few appear when blooming.
- *Styles.*—Columnar.
- *Length.*—Long.
- *Stigmas.*—Large.
- *Ovaries.*—Enclosed in calyx.

Plant:
- *Form.*—Herbaceous.
- *Growth.*—Medium.
- *Height.*—Medium.
- *Penduncle.*—Medium.

Foliage:
- *Color.*—Normal.
- *Size.*—Small.
- *Quantity.*—Large.
- *Shape.*—Pointed.
- *Texture.*—Normal.
- *Ribs and veins.*—Sharp-Lighter color.
- *Edges.*—Incurved.
- *Leaf underside.*—Rough with much hirsuteness.

In the description above color references are made to the "Horticultural Color Chart I & II" issued by the British Colour Council in collaboration with The Royal Horticultural Society, Copyright Robert F. Wilson, vol. I, 1938; vol. II, 1941, printed by Henry Stone and Son, Ltd., Banbury, England.

I claim:

1. A new and distinctive variety of Chrysanthemum as described and illustrated in the foregoing specification and accompanying drawings.

* * * * *